United States Patent [19]

Watanabe et al.

[11] 4,404,333
[45] Sep. 13, 1983

[54] THERMOPLASTIC POLYESTER RESIN, PRODUCTION OF SAME, AND ORTHOPEDIC CAST MATERIAL PRODUCED THEREFROM

[75] Inventors: Shoji Watanabe, Ohtake; Michio Nakanishi, Niiza, both of Japan

[73] Assignee: Daicel Chemical Industries, Inc., Osaka, Japan

[21] Appl. No.: 438,954

[22] Filed: Nov. 3, 1982

[30] Foreign Application Priority Data

Nov. 6, 1981 [JP] Japan ............................ 56-178808
Nov. 6, 1981 [JP] Japan ............................ 56-178809

[51] Int. Cl.³ ................... C08F 283/00; C08G 63/76
[52] U.S. Cl. .................................... 525/437; 128/90; 428/255; 428/290; 428/480; 528/274; 560/127; 528/283; 528/295.3; 528/302; 528/303
[58] Field of Search ............... 525/437; 528/274, 283, 528/295.3, 302, 303; 428/255, 290, 480; 128/90; 560/127

[56] References Cited

U.S. PATENT DOCUMENTS 3,692,023 9/1972 Phillips et al. .................... 128/90
3,773,595 11/1973 Burba et al. .................... 528/302 X Primary Examiner—Lucille M. Phynes
Attorney, Agent, or Firm—Hubbell, Cohen, Stiefel & Gross

[57] ABSTRACT

New thermoplastic polyester resins having a low melting point which are useful as a molding material, especially as an orthopedic cast material; said resin having the formula (I):

$$[A]_l[B]_m[C]_n \qquad (I)$$

where A denotes a residue of a straight or branched aliphatic dicarboxylic acid having 4 to 12 or 36; Carbon atoms B denotes a residue of a straight or branched aliphatic diol having 2 to 18; Carbon atoms C denotes a residue of 6-hydroxycaproic acid; these residues are linked through the ester bond and distributed randomly and/or in block in the molecule; $l$, $m$, and $n$ each has a value greater than 0; the residue of the 6-hydroxycaproic acid is 60 to 98 wt % and the sum of the residues of the aliphatic dicarboxylic acid and aliphatic diol is 40 to 2 wt %; the residue of the aliphatic dicarboxylic acid and the residue of the aliphatic diol are present in equimolar amount; and having a number-average molecular weight of 5,000 to 200,000.

16 Claims, No Drawings

THERMOPLASTIC POLYESTER RESIN, PRODUCTION OF SAME, AND ORTHOPEDIC CAST MATERIAL PRODUCED THEREFROM

BACKGROUND OF THE INVENTION

1. Field of the Invention

The present invention relates to a new thermoplastic polyester resin, a process for producing the same, and an orthopedic cast material produced therefrom. More particularly, this invention relates to a new thermoplastic polyester resin having a low melting point which is useful as a molding material, especially as an orthopedic cast material, a process for producing the same, and an orthopedic cast material produced therefrom.

2. Description of the Prior Art

Heretofore, calcined gypsum has been in general use as the orthopedic cast material to immobilize the broken limb and joint. However, this cast material is undesirable for patients because it is heavy, bulky, and soluble in water. In order to overcome these disadvantages, there has been developed an orthopedic cast material made of thermoplastic resin impregnated into a backing web such as a gauze and reticulate knitted or woven fabric, and polycaprolactone of high molecular weight has been proposed as such a thermoplastic resin (U.S. Pat. No. 3,692,023). This polymer, however, has a disadvantage that it has to be made soft, prior to application to a patient, by heating to a temperature above 60° C. which is the melting point of this polymer. This heat causes pain to the doctor and patient. To alleviate pain, it is considered to lower the melting point, and the heating temperature accordingly, by adding a plasticizer to the polymer. However, the plasticizer will cause another problem. That is, it harms the skin and lowers the mechanical strength of the resulting cast material. This is particularly true when an ester-type plasticizer is used. Under these circumstances, there has been a demand for a plastic cast material that can be applied at a temperature below 60° C.

The present inventors carried out a series of researches on this subject. As the result, it was found that a new thermoplastic polyester resin prepared by copolymerizing a specific aliphatic dicarboxylic acid, a specific aliphatic diol, and polycaprolactone of high molecular weight has a melting point lower than 60° C. and has strength high enough for use as cast material. The present invention is based on this finding.

SUMMARY OF THE INVENTION

It is an object of this invention to provide a thermoplastic polyester resin and a cast material produced therefrom, said thermoplastic polyester resin being represented by the formula $$[A]_l[B]_m[C]_n \qquad \ldots (I)$$

(where A denotes a residue of straight or branched aliphatic dicarboxylic acid of carbon number 4 to 12 or 36; B denotes a residue of straight or branched aliphatic diol of carbon number 2 to 18; C denotes a residue of 6-hydroxycaproic acid; these residues are linked through the ester bond and distributed randomly and/or in block in the molecule; l, m, and n each has a value greater than 0; the residue of the 6-hydroxycaproic acid is 60 to 98 wt% and the sum of the residues of the aliphatic dicarboxylic acid and aliphatic diol is 40 to 2 wt%, and the residue of the aliphatic dicarboxylic acid and the residue of the aliphatic diol are contained in the equimolar amount) and having a number-average molecular weight of 5,000 to 200,000.

DESCRIPTION OF THE PREFERRED EMBODIMENTS

The number-average molecular weight of the resin as used in this specification means the value obtained by gel permeation chromatography (GPC) under the following conditions.

Measuring conditions:
Apparatus: LC-3A (made by Shimadzu Seisakusho Ltd.)
Solvent: Tetrahydrofuran (flow rate: 1 ml/min)
Temperature: Room temperature
Detector: Shodex RI SE-11 (made by Showa Denko K. K.)
Column: HSG-PRE (one), HSG-20 (one), HSG-15 (three), and HSG-10 (one) (made by Shimadzu)

The term "random and/or block" means that the residues are all linked randomly, the residues are linked randomly, partly in block, and the residues are linked in block. The polyester resin of this invention contains the component C in an amount of 60 to 98 wt% in the copolymer, and has a number-average molecular weight of about 5000 to 200,000. The components A and B constitute the remainder or 40 to 2 wt% of the copolymer, and are contained in the equimolar amount. The values of l, m, and n are each greater than 0.

The acid corresponding to the aliphatic dicarboxylic acid residue constituting the component A in the formula (I) includes succinic acid, maleic anhydride, glutaric acid, adipic, acid, sebacic acid, azelaic acid, dodecane-2 acid, and dimer acid. Preferable among them is adipic acid. The residue A may be composed of two or more kinds of dicarboxylic acid residues.

The diol corresponding to the component B in the formula (I) includes ethylene glycol, propylene glycol, 1,4-butanediol, 2-methylpropanediol, 1,3-butylene glycol, diethylene glycol, neopentyl glycol, 1,6-hexane glycol, neopentyl glycol hydroxypivalic ester, 1,4-cyclohexane dimethanol, hydrogenated bisphenol A, and 1,2-dodecanediol. Preferable among them are branched diols such as propylene glycol, 2-methylpropanediol, 1,3-butyleneglycol, and neopentyl glycol, and oxygen-linked diols such as diethylene glycol. They are effective to lower the melting pont of the resulting resin. The residue B may be composed of two or more kinds of aliphatic diol residues.

The component C, the residue of 6-hydroxycaproic acid in the formula (I) should preferably be one which is derived from ε-caprolactone. It may also be derived from 6-hydroxycaproic acid itself. The content of the 6-hydroxycaproic acid residue should be 60 to 98 wt%, preferably 70 to 95 wt%, more preferably 80 to 95 wt%. If it is more than 98 wt%, the melting point of the resulting polymer does not decrease below 60° C.; and if it is less than 60 wt%, the melting point decreases excessively and the resulting resin becomes excessively soft, losing the mechanical strength required for cast material.

The melting point of the resin should be 40 to 58° C., preferably 45° to 56° C. The number-average molecular weight should be 5,000 to 200,000, preferably 10,000 to 150,000, and more preferably 20,000 to 80,000. If the molecular weight is excessively low, the resulting resin is low in mechanical strength, and if it is excessively high, the resulting resin is excessively high in melt viscosity, impairing the workability in the production of cast material and other molding materials.

The thermoplastic polyester resin of this invention can be prepared by heating with stirring and removal of water formed, for esterification reaction and polycondensation, the predetermined quantities of (i) ε-caprolactone or hydroxycaproic acid, (ii) diol component composed of one or more than one kind of linear or branched aliphatic diol of carbon number 2 to 18, and (iii) acid component composed of one or more than one kind of straight or branched aliphatic carboxylic acid or anhydride thereof or lower alkyl ester thereof of carbon number 4 to 12 or 36, in the presence of an esterification catalyst. To put it concretely, the synthesis is performed by mixing an aliphatic diol, an aliphatic dicarboxylic acid or anhydride thereof or lower alkyl ester thereof, and ε-caprolactone in prescribed quantities, adding an esterification catalyst, and heating the mixture with stirring at 150° to 230° C. under normal pressure or reduced pressure, while removing water formed, to effect esterification reaction and ring-opening addition polymerization of ε-caprolactone. In the later stage of the reaction, the temperature should be raised to 200 to 230° C. and the pressure should be reduced to remove unreacted diol and low-molecular weight reaction products as well as water.

The esterification catalyst is not specifically restricted, but it includes organotitanium compounds such as tetramethoxytitanium, tetraethoxytitanium, tetra-n-propoxytitanium tetraisopropoxytitanium, and tetrabutoxytitanium; organotin compounds such as di-n-butyltin dilaurate, di-n-butyltin oxide, and dibutyltin diacetate; and a combination of magnesium, calcium, or zinc acetate and antimony oxide or a titanium compound as mentioned above. The catalyst should preferably be used in an amount of 10 to 10,000 ppm based on the total polymer to be produced.

The reaction temperature should not be higher than 230° C., because polycaprolactone is depolymerized at 230° C. or more, with the result that the molecular weight does not increase any longer. The aliphatic dicarboxylic acid or anhydride thereof or lower alkyl ester thereof and the aliphatic diol to be actually used are selected from the above-mentioned acid components, anhydrides thereof, or $C_1$ to $C_3$ alkyl esters thereof, and diols.

The thermoplastic polyester resin of this invention can be produced by charging the raw materials all at once. However, the resin having a molecular weight greater than 5,000 can be produced more efficiently by the following method.

The above-mentioned diol component (ii) and acid component (iii) are mixed previously and subjected to esterification reaction and polycondensation in the presence of an esterification catalyst to produce a linear polyester having a molecular weight of about 5,000 to 100,000. Then, the above-mentioned ε-caprolactone is added in a prescribed amount, and the mixture is heated for reaction in the presence of a catalyst for polymerization and ring opening. For example, an aliphatic diol, an aliphatic dicarboxylic acid or an anhydride thereof or a lower alkyl ester thereof, and an esterification catalyst are mixed in the aforementioned ratio. The reactants are subjected to esterification reaction and polycondensation reaction at 150° to 280° C. under normal pressure and then under a reduced pressure of 10 mmHg or lower, to synthesize a linear polyester resin having a molecular weight of 2,000 to 100,000. Then, ε-caprolactone is added in a prescribed ratio and a catalyst is added for ring opening polymerization of ε-caprolactone. Reaction is carried out at 100° to 220° C. under normal pressure. Thus, the resin of this invention can be prepared. According to this method, as the polymer of ε-caprolactone is formed, the ester interchange takes place between the polycaprolactone and the linear polyester (molecular weight 2,000 to 100,000) added to the reaction system. Thus, the low-melting thermoplastic polyester resin of this invention is formed. In addition, according to this method, it is not necessary to stir a viscous resin of high degree of polymerization for a long time under reduced pressure. This is industrially advantageous.

The esterification catalyst used in the this method is as mentioned above. The catalyst for ring opening polymerization includes, for example, stannous halide such as stannous chloride, stannous bromide, and stannous iodide, and preferable among them is stannous chloride. This catalyst is added in an amount of 10 to 5,000 ppm, preferably 50 to 500 ppm. The reaction is remarkably accelerated when oxygen is present in the reaction system.

The ε-caprolactone and hydroxycaproic acid used in this invention should be pure in such a degree that substances containing water and active hydrogen as impurities are less than 0.05%. Substances containing active hydrogen work as a polymerization initiator under the reaction conditions mentioned above. Thus, if they are present more than 0.05%, the resulting polymer is low in the degree of polymerization.

The thermoplastic polyester resin of this invention obtained as above has a molecular weight of about 5,000 to 200,000. The melting point as used in this specification means the temperature at which the opaque resin becomes transparent in a heating medium.

The thermoplastic polyester resin of this invention can be used preferably for injection molding and extrusion molding. Having a melting point lower than 60° C., it can be used preferably as an orthopedic cast material. In the latter case, the thermoplastic polyester resin may be formed into a sheet which is used directly as a cast material, or may be supported by a proper substrate before being used as a cast material. The resin may be incorporated with additives such as colorant and filler. To put it more concretely, the resin is incorporated with an inorganic compound such as titanium oxide as a colorant or filler, and then dispersed or dissolved in a proper solvent. The resulting solution is impregnated into or applied to and/or fusion bonded to a backing substrate such as gauze, nonwoven fabric, and reticulate woven cloth. A preferred backing substrate is a reticulate substrate as disclosed in British Pat. No. 1,522,399.

The impregnation of backing substrate may be accomplished by immersing the substrate in the polymerization system in which the polyester resin of this invention is being produced.

The cast material prepared as mentioned above is lighter and less bulky than the conventional one made of calcined gypsum. In addition, it is waterproof and the patient can take a bath with a splint made of it on. Moreover, the cast material softens and melts at a temperature lower than that of the conventional cast material made of caprolactone polymer. This makes handling easy and relieves the patient of burn.

The invention is now described with reference to the following nonlimitative examples. Quantities are expressed as parts by weight.

EXAMPLES 1 TO 4 AND COMPARATIVE EXAMPLE 1 (PRODUCTION)

In a four-necked flask equipped with a nitrogen inlet, thermometer, condenser for removal of water formed by esterification, and stirrer were placed 5840 parts of adipic acid, 4785 parts of diethylene glycol, and 1 part of tetrabutyl titanate. Reaction was carried out under the nitrogen stream at 150° C. gradually elevating to 230° C. for 10 hours with stirring, while removing water formed by the esterification reaction. Reaction was continued at 230° C. for 3 hours under a reduced pressure of 250 to 5 mmHg and then for 3 hours under a reduced pressure of 5 mmHg to remove unreacted matters, water, and low molecular weight substance. Thus, there was obtained a liquid polyester (diethylene glycol adipate polyester) having a number-average molecular weight of 10,500 which flows very little at room temperature. This polyester was dissolved in a prescribed quantity of ε-caprolactone (ε-CL) and stannous chloride was added as a catalyst. The reactants were heated to 140° C. and air was blown into the reactants for one minute. Reaction was carried out under the nitrogen stream at 140° C. gradually elevating to 220° C. for 8 hours. Thus, there was obtained a thermoplastic polyester resin. The properties of the resulting resin are shown in Table 1.

TABLE 1

| | Comparative Example | Examples | | | |
|---|---|---|---|---|---|
| | 1 | 1 | 2 | 3 | 4 |
| Composition | | | | | |
| Diethylene glycol adipate (parts) | 0 | 5 | 10 | 20 | 30 |
| ε-CL (parts) | 100 | 95 | 90 | 80 | 70 |
| SnCl$_2$ (ppm) | 100 | 100 | 100 | 100 | 100 |
| Properties | | | | | |
| Melting point (°C.) | 60 | 58 | 56 | 52 | 47 |
| Tensile strength (kg/cm$^2$) | 210 | 195 | 190 | 80 | 50 |
| Elongation (%) | 544 | 630 | 649 | 130 | 4 |
| Number-average molecular weight | 75000 | 73000 | 65000 | 54000 | 47000 |

EXAMPLE 5 AND COMPARATIVE EXAMPLE 2 (CAST MATERIAL)

Each of the thermoplastic polyester resins produced in Examples 2 to 4 was dissolved in toluene to prepare 30% solution. The solution was applied to a gauze bandage, followed by drying. The resulting bandage was heated in warm water at 58° C. and then wound around a finger so that the layers are fusion bonded. After cooling at room temperature, a hard cast was formed. This cast was found to have sufficient strength, rigidity, and flexibility required for cast.

On the other hand, a cast was prepared in the same way as above from the thermoplastic polyester resin obtained in Comparative Example 1. A difficulty was encountered in its application to a finger due to its high melting point.

EXAMPLE 6 (PRODUCTION)

In a four-necked flask equipped with a nitrogen inlet, thermometer, condenser for removal of water formed by esterification, and stirrer were placed 292 parts of adipic acid, 208 parts of 2-methylpropanediol, 3980 parts of ε-caprolactone, and 0.04 part of tetrabutyl titanate. Reaction was carried out under the nitrogen stream at 150° C. gradually elevating to 220° C. After the time when water was not distilled any longer under normal pressure, condensation reaction was performed for 1 hour under a reduced pressure of 250 mmHg, for 3 hours under 5 mmHg, and for 8 hours under 1 mmHg at 220° C. Thus, there was obtained a polyester resin having a number-average molecular weight of 23,000.

EXAMPLE 7 (PRODUCTION)

In a four-necked flask equipped with a nitrogen inlet, thermometer, condenser for removal of water formed by esterification, and stirrer were placed 292 parts of adipic acid, 240 parts of neopentyl glycol, and 0.005 part of tetrabutyl titanate. Esterification reaction was carried out at 150° C. gradually elevating to 240° C. After the time when water was not distilled any longer under normal pressure, the pressure was reduced from 250 mmHg to 5 mmHg and condensation reaction was performed for 5 hours under 5 mmHg. Thus, there was obtained a highly viscous liquid resin. This resin was dissolved in 270 parts of ε-caprolactone and 0.06 part of stannous chloride was added as a catalyst. The reactants were heated to 140° C. and air was blown into the reactants for one minute. Reaction was carried out under the nitrogen steam at 140° C. gradually elevating to 220° C. for 8 hours. Thus, there was obtained a thermoplastic polyester resin having a melting point of 55° C. and a number-average molecular weight of 31,000.

EXAMPLE 8 (PRODUCTION)

In the same apparatus as used in Example 1 were placed 564 parts of azelaic acid, 330 parts of neopentyl glycol, and 0.09 part of tetrabutyl titanate. Esterification reaction was carried out under the nitrogen stream while heating from 150° to 230° C. gradually and removing water formed by the reaction. After the time when water was not distilled any longer under normal pressure, the condensation reaction was continued for 8 hours under a reduced pressure from 250 mmHg to 10 mmHg. Thus, there was obtained a highly viscous polyester resin having a molecular weight of 13,000. This resin was dissolved in 950 parts of ε-caprolactone and 0.3 part of stannous bromide was added as a catalyst. After reaction at 200° C. for 8 hours, there was obtained a thermoplastic polyester resin having a melting point of 56° C. and a number-average molecular weight of 73,000.

EXAMPLE 9 (PRODUCTION)

In the same apparatus as used in Example 1 were placed 460 parts of dodecane dicarboxylic acid, 230 parts of neopentyl glycol, 7000 parts of ε-caprolactone, 0.4 part of tetrabutyl titanate, and 1.5 parts of stannous chloride. The temperature was raised from 150° C. to 220° C. to carry out esterification reaction. Condensation reaction was carried out at 220° C. under 10 mmHg for 10 hours, while removing the distillate. Thus, there was obtained a thermoplastic polyester resin having a melting point of 56° C. and a number-average molecular weight of 48,000.

EXAMPLE 10 (PRODUCTION)

In the same apparatus as used in Example 1 were placed 280 parts of dimer acid obtained from linoleic acid, 70 parts of ethylene glycol, 4500 parts of ε-caprolactone, 0.5 part of tetrabutyl titanate, and 0.5 part of stannous chloride. Esterification reaction was performed at 180° C. for 5 hours and then at 220° C. for 5 hours. Condensation reaction was carried out at 220° C. under 10 mmHg for 10 hours, while removing the distillate. Thus, there was obtained a thermoplastic polyester resin having a melting point of 56° C. and a number-average molecular weight of 59,000.

EXAMPLE 11 (CAST MATERIAL)

Each of the thermoplastic polyester resins in the form of pellets obtained in Examples 6 to 9 was formed into a 3 mm thick sheet by a hot press. The resulting sheet was heated to 56° C. and then pressed against a finger to be formed into the contour of the finger, followed by cooling at room temperature. The cast thus prepared protected the finger from external force, functioning as a splint.

EXAMPLE 12 (CAST MATERIAL)

The composition of 95% of the thermoplastic polyester resin obtained by Example 2 and 5% of titanium oxide was melted and applied to a reticulate woven cloth having openings of 3 mm × 5 mm by using a calendering machine, to obtain a cast material. 80 parts by weight of the composition was supported on 20 parts by weight of the substrate of reticulate woven cloth.

What we claim is:

1. A thermoplastic polyester resin having the formula (I):

$$[A]_l[B]_m[C]_n \ldots \qquad (I)$$

where A denotes a residue of a straight or branched aliphatic dicarboxylic acid having 4 to 12 or 36; carbon atoms B denotes a residue of a straight or branched aliphatic diol having 2 to 18; carbon atoms C denotes a residue of 6-hydroxycaproic acid; these residues are linked through the ester bond and distributed randomly and/or in block in the molecule; l, m, and n each has a value greater than 0; the residue of the 6-hydroxycaproic acid is 60 to 98 wt% and the sum of the residues of the aliphatic dicarboxylic acid and aliphatic diol is 40 to 2 wt%; and the residue of the aliphatic dicarboxylic acid and the residue of the aliphatic diol are present in equimolar amount; and having a number-average molecular weight of 5,000 to 200,000.

2. A resin of claim 1 in which the number-average molecular weight is 10,000–150,000.

3. A resin of claim 1 in which the number-average molecular weight is 20,000–80,000.

4. A resin of claim 1 in which the residue of the hydroxycaproic acid is 70–95 wt% and the sum of the residues of the aliphatic dicarboxylic acid and aliphatic diol is 30–5 wt%.

5. A resin of claim 1 in which the residue of the hydroxycaproic acid is 80–95 wt% and the sum of the residues of the aliphatic dicarboxylic acid and aliphatic diol is 20–5 wt%.

6. A resin of claim 1 in which A in the formula (I) is a residue of succinic acid, maleic anhydride, gultaric acid, adipic acid, sebacic acid, azelaic acid, dodecane-2 acid or dimer acid, or residues of their mixtures.

7. A resin of claim 6 in which A is a residue of adipic acid.

8. A resin of claim 1 in which B in the formula (I) is a residue of ethylene glycol, propylene glycol, 1,4-butanediol, 2-methylpropanediol, 1,3-butylene glycol, diethylene glycol, neopentyl glycol, 1,6-hexane glycol, neopenthyl glycol hydroxypivalic ester, 1,4-cyclohexane dimethanol, hydrogenated bisphenol A or 1,2-dodecanediol, or residues of their mixtures.

9. A resin of claim 8 in which B is diethylene glycol, propylene glycol, 2-methylpropanediol, 1,3-buthylene glycol or neopentyl glycol.

10. The use of a thermoplastic polyester resin according to claim 1 as an orthopedic cast material.

11. An use of claim 10, in which the thermoplastic polyester resin is impregnated into or applied to and/or fusion bonded to a backing substrate such as gauze, nonwoven fabric or reticulate woven cloth.

12. A process for the production of a thermoplastic polyester resin which comprises mixing (i) ε-caprolactone or 6-hydroxy-caproic acid, (ii) a straight or branched aliphatic diol having 2–18 carbon atoms and (iii) a straight or branched aliphatic dicarboxylic acid having 4–12 or 36 carbon atoms, or anhydride or lower alkyl ester thereof; and subjecting the mixture in the presence of a catalyst for esterification to an esterification and condensation.

13. A process of claim 12 in which the catalyst for esterification is an organotitanium compound such as tetramethoxytitanium, tetraethoxytitanium, tetra-n-propoxytitanium, tetraisopropoxytitanium, or tetrabutoxytitanium; an organotin compound such as di-n-butyltin dilaurate, di-n-butyltin oxide or dibutyltin diacetate; and a combination of magnesium, calcium, or zinc acetate and antimony oxide or an organotitanium compound as mentioned above.

14. A process of claim 12 in which the esterification and condensation is conducted at a temperature of 150°–230° C.

15. A process for the production of a thermoplastic polyester resin which comprises mixing (ii) a straight or branched aliphatic diol having 2–18 carbon atoms and (iii) a straight or branched aliphatic dicarboxylic acid having 4–12 or 36 carbon atoms, or anhydride or lower alkyl ester thereof; and subjecting the mixture in the presence of a catalyst for esterification to an esterification and condensation, to give a linear polyester resin having a number-average molecular weight of 2,000–100,000; and then reacting said polyester resin with (i) ε-caprolactone or 6-hydroxy-caproic acid in the presence of a catalyst for polymerization and ring opening.

16. A process of claim 15 in which the catalyst for ring opening polymerization is stannous halide such as stannous chloride, stannous bromide or stannous iodide.

* * * * *